United States Patent
Kamcharov et al.

(10) Patent No.: US 11,925,192 B2
(45) Date of Patent: *Mar. 12, 2024

(54) BEVERAGE WITH COLLAGEN AND ADDITIONAL ADDITIVES

(71) Applicant: WELLDRINKS LTD, Sofia (BG)

(72) Inventors: Alexander Evgenievich Kamcharov, Saint Petersburg (RU); Martin Seele, Dusseldorf (DE); Tihomir Georgiev Yovchev, Sofia (BG); Yavor Nikolaev Draganov, Rhodope (BG); Jurgen Pieck, Lutry (CH); Christian Schrobsdorff, Sofia (EG)

(73) Assignee: WELLDRINKS LTD, Sofia (BG)

( * ) Notice: Subject to any disclaimer, the term of this patent is extended or adjusted under 35 U.S.C. 154(b) by 0 days.

This patent is subject to a terminal disclaimer.

(21) Appl. No.: 14/969,519

(22) Filed: Dec. 15, 2015

(65) Prior Publication Data

US 2016/0205989 A1    Jul. 21, 2016

(30) Foreign Application Priority Data

Jan. 16, 2015 (BG) .......................................... 2935

(51) Int. Cl.
| | |
|---|---|
| A23L 2/66 | (2006.01) |
| A23L 2/44 | (2006.01) |
| A23L 2/52 | (2006.01) |
| A23L 2/54 | (2006.01) |
| A23L 2/56 | (2006.01) |
| A23L 2/58 | (2006.01) |
| A23L 2/60 | (2006.01) |
| A23L 2/68 | (2006.01) |
| A61K 8/65 | (2006.01) |
| A61K 9/00 | (2006.01) |
| A61K 38/01 | (2006.01) |
| A61K 38/39 | (2006.01) |
| A61Q 19/00 | (2006.01) |
| A61Q 19/08 | (2006.01) |

(52) U.S. Cl.
CPC ....... *A23L 2/66* (2013.01); *A23L 2/44* (2013.01); *A23L 2/52* (2013.01); *A23L 2/54* (2013.01); *A23L 2/56* (2013.01); *A23L 2/58* (2013.01); *A23L 2/60* (2013.01); *A23L 2/68* (2013.01); *A61K 8/65* (2013.01); *A61K 38/014* (2013.01); *A61K 38/39* (2013.01); *A61Q 19/007* (2013.01); *A61Q 19/08* (2013.01); *A23V 2002/00* (2013.01); *A61K 9/0095* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 5,424,082 A * | 6/1995 | Dake .................... | A23L 2/68 426/74 |
| 2003/0175398 A1 | 9/2003 | Ogasawara et al. | |
| 2009/0041897 A1* | 2/2009 | Gamay ................. | A23L 2/52 426/61 |
| 2009/0041911 A1* | 2/2009 | Gamay ................. | A23L 2/38 426/115 |
| 2010/0316768 A1 | 12/2010 | Stillman | |
| 2011/0151059 A1* | 6/2011 | Xu ........................ | A23L 1/3056 426/72 |
| 2014/0212565 A1 | 7/2014 | Bradley et al. | |
| 2015/0352045 A1 | 12/2015 | Raper et al. | |

FOREIGN PATENT DOCUMENTS

| | | |
|---|---|---|
| ES | 1210813 U | 4/2018 |
| JP | 2002027956 A | 1/2002 |
| JP | 2007167079 A | 7/2007 |
| JP | 2008194010 A | 8/2008 |
| RU | 2658380 C1 | 6/2018 |
| WO | 2004023899 A1 | 3/2004 |
| WO | 2007098593 A1 | 9/2007 |
| WO | 2013049540 A2 | 4/2013 |

OTHER PUBLICATIONS

Dybka et al. ("Collagen Hydrolysates as a new diet supplement"; Food Chemistry and Biotechnology, vol. 73(1058) 2009).*
Matheson ("ask . . . The Gas Professionals" copyright 2014).*
Hanover et al. ("Manufacturing, composition and applications of fructose"; Am J. clin Nutr 1993; 58(suppl): 724s-32s).*
Ravindra et al. ("Carbonated fermented dairy drink-effect on quality and shelf-life" J Food Sci Technol. Nov. 2014; 51 (11):3397-3403).*
Aito-Inoue M, Lackeyram D, Fan MZ et al., Transport of a tripeptide, gly-pro-hyp, across the porcine intestinal brush-border membrane, J Pept Sci (2007).

(Continued)

*Primary Examiner* — Julie Ha
*Assistant Examiner* — Tara L Martinez
(74) *Attorney, Agent, or Firm* — Gearhart Law, LLC; David Postolski

(57) ABSTRACT

The present invention concerns a beverage having water and a concentration range of about 0.001 grams per liter to 8.44 grams per liter of collagen, wherein the collagen is hydrolyzed. The collagen concentration range may be between 1 milligram per liter to about 8440 milligram per liter or 1 parts per million to about 8440 parts per million. The hydrolyzed collagen has collagen peptides. The collagen peptides are produced through hydrolysis of a plurality of collagen sources. The plurality of collagen sources are derived from at least one of animal raw materials, animals raised in non-organic or organic farms, animals from various animal species and various parts of the animal carcass. The water may be comprised of at least one of tap water, spring or mineral water, and iceberg or glacier water.

21 Claims, No Drawings

(56) References Cited

OTHER PUBLICATIONS

Jeremy M Berg, John L Tymoczko, and Lubert Stryer. New York—W H Freeman; Biochemistry (5th ed), Ch. 23.1.1 (2002).

Chung JH, Seo JY, Choi HR et al., Modulation of skin collagen metabolism in aged and photoaged human skin in vivo, J Invest Dermatol (2001).

Kawaguchi T, Nanbu PN, Kurokawa M., Distribution of prolylhydroxyproline and its metabolites after oral administration In rats, Biol Pharm Bull (2012).

Liang J, Pei X, Zhang Z et al., The protective effects of long-term oral administration of marine collagen hydrolysate from chum salmon on collagen matrix homeostasis in the chronological aged skin of sprague-dawley male rats, Journal of Food Science, vol. 75, No. 8 (2010).

Liu C, Sugita K, Nihei K et al., Absorption of hydroxyproline-containing peptides in vascularly perfused rat small intestine in situ., Biosci Biotechnol Biochem (2009).

Matsuda N, Koyama Y, Hosaka Y et al., Effects of ingestion of collagen peptide on collagen fibrils and glycosaminoglycans in the dermis, J Nutr Sci Vitaminol (Tokyo) (2006).

Oba C, Ohara H, Morifuji M et al. Collagen hydrolysate intake improves the loss of epidermal barrier function and skin elasticity induced by UVB irradiation in hairless mice. Photodermatol Photoimmunol Photomed, pp. 204-211 (2013).

Ohara H, Ichikawa S, Matsumoto H et al., Collagen-derived dipeptide, proline-hydroxyproline, stimulates cell proliferation and hyaluronic acid synthesis in cultured human dermal fibroblasts., J Dermatol (2010).

Pasquali-Ronchetti I, Baccarani-Contri M., Elastic Fiber During Development and Aging, Microsc Res Tech. (1997).

Quan T, Little E, Quan H et al. Elevated matrix metalloproteinases and collagen fragmentation in photodamaged human skin- impact of altered extracellular matrix microenvironment on dermal fibroblast function, J Invest Dermatol, (2013).

Ross, John R and Shaw, Margaret M, The Effect of Dehydration on The Pancreatic and Intestinal Enzymes by John R. Ross and Margaret M. Shaw (From the Department of Medical Research, Bunting Institute, University of Toronto, Toronto, Canada (1933).

Kligman AM, Zheng P, Lavker RM. The anatomy and pathogenesis of wrinkles., Br J Dermatol (1985).

Sakai S, Yasuda R, Sayo T et al., Hyaluronan exists in the normal stratum corneum, J Invest Dermatol (2000).

Schagen SK, Zampeli VA, Makrantonaki E et al., Discovering the link between nutrition and skin aging., Dermatoendocrinology (2012).

Shigemura Y, Kubomura D, Sato Y et al., Dose-dependent changes in the levels of free and peptide forms of hydroxyproline in human plasma after collagen hydrolysate ingestion, Food Chem (2014).

Shimizu J, Asami N, Kataoka A et al., Oral collagen-derived dipeptides, prolyl-hydroxyproline and hydroxyprolyl-glycine, ameliorate skin barrier dysfunction and alter gene expression profiles in the skin., Biochemical and Biophysical Research Communications (2015).

Shuster S, Black MM, McVitie E., The influence of age and sex on skin thickness, skin collagen and density, Br J Dermatol (1975).

Varani J, Dame MK, Rittie L et al., Decreased collagen production in chronologically aged skin-roles of age-dependent alteration in fibroblast function and defective mechanical stimulation, Am J Pathol (2006).

Verdier-Sévrain S, Bonté F., Skin hydration—a review on its molecular mechanisms., J Cosmet Dermatol (2007).

Watanabe-Kamiyama M, Shimizu M, Kamiyama S et al., Absorption and effectiveness of orally administered low molecular weight collagen hydrolysate in rats, J Agric Food Chem (2010).

Search Report dated Jul. 16, 2018 in corresponding European application No. 15877721.9.

Tomoko Okawa et al., "Oral administration of collagen tripeptide improves dryness and pruritus in the acetone-induced dry skin model", Journal of Dermatological Science, Elsevier, Amsterdam, NL; vol. 66, No. 2, Feb. 8, 2012, pp. 136-143.

Anonymous: "Cocoa Fruit Flavored Collagen Enhanced Sport Still Water", Nov. 1, 2014, URL: http://www.gnpd.com/sinatra/recordpage/2764481.

Anonymous: "EpiQ NAG Collagen Beverage", Dec. 1, 2014, URL: http://www.gnpd.com/sinatra/recordpage/2829239.

Written Opinion of the International Searching Authority, dated Mar. 23, 2021, for corresponding PCT Application No. PCT/IB2020/060620, International Filing Date of Nov. 11, 2020, consisting of 6 Pages.

International Search Report, dated Mar. 23, 2021, for corresponding PCT Application No. PCT/IB2020/060620, International Filing Date of Nov. 11, 2020, consisting of 11 Pages.

Sarah Guerin, et. al. "Deconstructing collagen piezoelectricity using alanine-hydroxyproline-glycine building blocks," Nanoscale, 2018, 10(20), pp. 9653-9663.

Aaron L. Fidler, et. al. "The triple helix of collagens—an ancient protein structure that enabled animal multicellularity and tissue evolution," Journal of Cell Science, 2018, 131(7), 10.1242/jcs.203950.

Thengiz V. Burjanadze and Arthur Veis. "A Thermodynamic Analysis of the Contribution of Hydroxyproline to the Structural Stability of the Collagen Triple Helix," Connective Tissue Research, 1997, 36(4), pp. 347-365.

Alberts B, Johnson A, Lewis J, et al. "The Shape and Structure of Proteins," Molecular Biology of the Cell. 4th edition. New York: Garland Science; 2002. Available from: https://www.ncbi.nlm.nih.gov/books/NBK26830/.

Renny T. Franceschi, et. al. "Effects of ascorbic acid on collagen matrix formation and osteoblast differentiation in murine MC3T3-E1 cells," J Bone Miner Res, 1994, 9, pp. 843-854.

David A. Swann and Stuart S. Sotman. "The chemical composition of bovine vitreous-humour collagen fibres," Biochem J, 1980, 185(3), pp. 545-554.

Ronald R. Miner. Collagen metabolism: a comparison of diseases of collagen and diseases affecting collagen. Am J Pathol. 1980, 98(1), pp. 225-280.

Kelly L. Gorres and Ronald T. Raines. "Prolyl 4-hydroxylase," Critical Reviews in Biochemistry and Molecular Biology, 2010, 45(2), pp. 106-124.

Eikichi Suzuki, et. al. "Role of hydroxyproline in the stabilization of the collagen molecule via water molecules," International Journal of Biological Macromolecules, 1980, 2(1), pp. 54-56.

Matthew D. Shoulders and Ronald T. Raines. "Collagen Structure and Stability," Annu. Rev. Biochem., 2009, 78, pp. 929-958.

A. J. Cowieson, et. al. "Interactive effects of dietary protein concentration, a mono-component exogenous protease and ascorbic acid on broiler performance, nutritional status and gut health," Animal Production Science, 2017, 57, pp. 1058-1068.

Mengmeng Feng and Mirko Betti. "Transepithelial transport efficiency of bovine collagen hydrolysates in a human Caco-2 cell line model," Food Chemistry, 2017, 224, pp. 242-250.

Linda K. Hansen. et. al. "Regulation of Hepatocyte Cell Cycle Progression and Differentiation by Type I Collagen Structure," Current Topics in Developmental Biology, 2005, 72, pp. 205-236.

Yasushi Sato, et. al. "Synergistic effect of ascorbic acid and collagen addition on the increase in type 2 collagen accumulation in cartilage-like MSC sheet," Cytotechnology, 2017, 69, pp. 405-416.

Juliet M. Pullar, et. al. "The Roles of Vitamin C in Skin Health," Nutrients, 2017, 9(8). 10.3390/nu9080866.

Nicholas N. DePhillipo, et. al. "Efficacy of Vitamin C Supplementation on Collagen Synthesis and Oxidative Stress After Musculoskeletal Injuries: A Systematic Review," Orthopaedic Journal of Sports Medicine, 2018, 6(10). 10.1177/2325967118804544.

Arthur D. Conigrave and Edward M. Brown. "Taste Receptors in the Gastrointestinal Tract II. l-Amino acid sensing by calcium-sensing receptors: Implications for GI physiology," American Journal of Physiology-Gastrointestinal and Liver Physiology, 2006, 291, 5, pp. G753-G761.

Steven C. Hebert, et. al. "Functions and roles of the extracellular Ca2+-sensing receptor in the gastrointestinal tract," Cell Calcium, 2004, 35(3), pp. 239-247.

(56) References Cited

OTHER PUBLICATIONS

Chrysoula Argyrou, et. al. "Effect of calcium and vitamin D supplementation with and without collagen peptides on bone turnover in postmenopausal women with osteopenia," J Musculoskelet Neuronal Interact., 2020, 20(1), pp. 12-17.

Michael Roth, et. al. "Ca2+ channel blockers modulate metabolism of collagens within the extracellular matrix," Proceedings of the National Academy of Sciences, 1996, 93(11), pp. 5478-5482.

* cited by examiner

BEVERAGE WITH COLLAGEN AND ADDITIONAL ADDITIVES

CLAIM OF PRIORITY

This application claims priority to Bulgarian Utility Model No. 2935 filed on Jan. 16, 2015, the contents of which are fully incorporated herein by reference.

FIELD OF THE EMBODIMENTS

This invention characterizes beverages comprising hydrolysed collagen, derived from animal raw materials. Those raw materials may be various according to their origin, namely, animals it is derived from may be raised in non-organic farms or organic farms of freely captured ones, animals may be from various animal species, as for example: single and cloven-hoofed mammals, fish, birds, snails; or may be derived from various parts of the carcass.

BACKGROUND OF THE EMBODIMENTS

The beneficial properties of collagen are uncountable and they are applicable both in the medical field and with regard to the aesthetics. Collagen is a major protein in the human connective tissue, while its concentration varies in different body parts: cartilages, cornea, arteries, and skin. Robust and inextensible, possessing a great tensile strength, it is the principal component of cartilages, tendons and articular joints, bones and teeth. Also, collagen is the building material for the blood vessel walls—capillaries, veins, arteries. It imparts to them strength and energy, structure and flexibility for the effective transport of blood to each single cell. Collagen is of vital importance for muscle functioning. The collagen molecules provide the muscle fibers with power and structure, which are necessary for their functioning all day long. Collagen not only builds up the muscle fibers, but also the smooth muscles—the cardiac muscle, the bladder muscles and the genitalia muscles.

Collagen reproduces permanently by itself in the human body. However, after the age of 25 this process decelerates and progressively slackens with advancing age. Disorders of collagen buildup can also be provoked in situations of permanent overloading (for example in power sports, or in case of intensive physical activity). The decrease in collagen is due to collage progressively running low, or the decrease owing to slowed down biosynthesis with the passing of the years evokes aging of soft tissues and bones (osteoporosis). The collagen deficit, rising with advancing age, leads to visible uncomfortable effects, like: skin drying and wrinkling, limited mobility due to stiffness and joint pain, frequent fractures, provoked by osteoporotic changes, the appearance of pointed and visible capillaries on the skin surface, as well as a distressing worsened state of varicose veins.

In its original state, the collagen molecule is very difficult to degrade by the digestive system owing to its great length. Therefore, in case of additional administration of collagen, a product must be selected, wherein the collagen is "cut off", i.e. "hydrolyzed" beforehand, whereby it's considerably better assimilation by the organism is ensured. Moreover, the consequent benefits are enhanced in this way. Collagen can be administered in the form of tablets, capsules, or in the form of a drink The collagen drinks are known in Japan and in the West for a long time and only now they begin to enter Europe en masse, owing to their proven among consumers effect on beauty and health, inclusive joints.

Recent scientific studies show, that the liquid collagen form for drinking is absorbed by the organism at levels more than 90%, which is absolutely unachievable when collage is either in tablet or capsule form. The liquid collagen form has demonstrated better results, higher efficiency of active ingredients and unrivalled absorption. Moreover, all dietary supplement forms—tablets, capsules, sachets etc. definitely burden more on the digestive system, in contrast to the liquid form for drinking, which is easily assimilated by the stomach. The accurate dosage is of particular importance for the consumers of collagen drinks.

All collagen drinks that are known, have a different percentage of hydrolyzed collagen and additives like aromatizes, vitamins, stabilizers etc. Another benefit of the created drink is that it practically doesn't allow any additional burden on the organism by unnatural chemical additives, like preservatives, aromatizers, artificial colors, flavor enhancers etc., These components are put in products with more concentrated amount of added hydrolyzed collagen. The absence of any additional components, except drinking water and hydrolyzed collagen, in the offered new product represents an important benefit, which ensures its administration without limitations regarding age and health state of the expected consumers. The risk of forming intolerance, or exacerbation of hyperaesthesia of the organism, which normally is provoked by additionally added unnatural chemical additives, is completely avoided. In the present invention, the optimal concentration of hydrolyzed collagen in the drink is completely clear in taste and almost wholly corresponding to the neutral taste of the clean drinking water. Furthermore, the drink is maximal simplified in functionally and that is why it doesn't burden on the consumer with additional calories. As a whole, the consumption of the created non-carbonated alcohol-free drink leads to the improvement of the skin structure, the skin density and the skin turgor; to the improvement of the muscle tone; as well as to the improvement of the condition and the flexibility of the articulations.

The market offers a wide variety of beverages containing various healthy ingredients. There is a natural strive of the contemporary society to improve its nutrition through including food and beverages with high added value, provided by the various forms of ingredients, beneficial for the body, included in their contents. This way, the need of consumers to reach better shape and tonus, to live a full life, feel good and preventively enhance their health can be satisfied. Beverages, which include in their content hydrolysed collagen, may be offered in convenient and easy for consumption form. The collagen in these drinks may be a source of valuable proteins in the body that can characterize with high and full assimilation. At the same time, when collagen is added in beverages, it combines the advantage, the daily intake of fluids to be stimulated, which usually is what underlies most recommended healthy diets. The sufficient intake of fluids is extremely important for many groups of people having specific and increased needs of fluids, such as, active athletes or people whose work and life comprise high physical activity or mental pressure. The additional intake of hydrolysed collagen is a valuable source of one's daily nutrition. Also, collagen offers one a full set of all amino acids needed for the synthesis of collagen matrix in the human body. This is particularly important for active people, the elderly, pregnant and lactating women, people undergoing aesthetic surgery and others.

Specific references to relevant prior art are herein described as follows:

U.S. Patent Publication No. 2010/0316768 and International Patent Publication No. WO2004023899 disclose a shelf-stable, ready to use, water-like composition for humans/animals; as an adjunct to fiber-water, and/or safe drinking water, consumed directly, tube feedings, or in the preparation/reconstitution of food(s)/beverage(s). These disclosures teach a fortified fiber-water with added delivery systems: Encapsulations/particles, of different size(s), shape(s), material(s), colors, non-visible, serving one or more functions: improved taste, odor-masking; controlled release applications; bio-availability of actives, avoid hygroscopicity; minimized interactions, improved thermal, oxidative, and shelf-life; decorative.

U.S. Patent Publication No. 2014/0212565 and International Patent Publication No. WO2013049540 teach a clear high protein beverage comprising: water; between about 4% and about 8% by weight protein; and a flavorant. WO2007098593 teaches an alkaline soluble fiber compositions and methods for preparing the same. Soluble fiber for use in the compositions of the invention is contributed from one or more sources and is preferably inulin, FOS and/or scFOS. In some cases the compositions have a pH of between 8.0 and 9.5.

Various method and solutions are known in the art. However, they are substantially different from the present disclosure. The other inventions fail to solve all the problems taught by the present disclosure, a beverage with the beneficial properties of collagen.

SUMMARY OF THE EMBODIMENTS

The present invention concerns a beverage having water and a concentration range of about 0.001 grams per liter to 8.44 grams per liter of collagen, wherein the collagen is hydrolyzed. The collagen concentration range may be between 1 milligram per liter to about 8440 milligram per liter or 1 parts per million to about 8440 parts per million. The hydrolyzed collagen has collagen peptides. The collagen peptides are produced through hydrolysis of a plurality of collagen sources. The plurality of collagen sources are derived from at least one of animal raw materials, animals raised in non-organic or organic farms, animals from various animal species and various parts of the animal carcass. The water may be comprised of at least one of tap water, spring or mineral water, and iceberg or glacier water. The beverage may be carbonated or non-carbonated.

The present invention concerns a beverage having water, a concentration range of about 0.001 grams per liter to 8.44 grams per liter of collagen; and at least one additive. The additive may be a stabilizing preservative. The stabilizing preservative may have chemical substances which dissolute in the beverage and are only parts of its content or have chemically active substances used in the production of the beverage but subsequently dissolute to other ingredients. The additive may be a preservative. The beverage may be pasteurized via a plurality of methods. The additive may be a packaging gas and/or a colorant. The colorant may be synthetic or organic and derived from vegetable, fruit or animal origin. The colorant may have a concentration range of at least one of 0.0001% to about 0.05%, 0.001% to about 0.1%, and 0.003% to about 0.2%. The additive may be a plurality of sweeteners. The sweeteners may be at least one of liquid form, hard form, natural sugars, refined sugars, low caloric, and non refined sugars. The additive may be a plurality of fruit juices or fruit juice concentrates. The beverage of claim 11 wherein the at least one additive comprises at least one of a plurality of vegetable juices or vegetable juice concentrates. The additive may be a plurality of acidity regulating or E-number additives. The additive may be a plurality of thickeners. The additive may be a plurality of stabilizers. The additive may be a plurality of flavor enhancers. The additive may be a plurality of vitamins. The additive may be a plurality of minerals. The additive may be a plurality of electrolytes. The additive may be a plurality of amino acids. The additive may be at least one other protein with a concentration range sum total of 0.0001 grams per liter to 8.44 grams per liter. The additive may be a plurality of dairy components. The additive may be a plurality probiotic ingredients. The additive may be a plurality prebiotic ingredients. The additive may be a plurality of extracts. The beverage may be carbonated or non-carbonated.

DESCRIPTION OF THE PREFERRED EMBODIMENTS

The preferred embodiments of the present invention will now be described. Reference will now be made in detail to each embodiment of the present invention. Such embodiments are provided by way of explanation of the present invention, which is not intended to be limited thereto. In fact, those of ordinary skill in the art may appreciate upon reading the present specification that various modifications and variations can be made thereto.

This invention regards to beverages comprising functional ingredient hydrolysed collagen in concentration: from 0.001 g/L g/L to 8.44 g/L, which may also be expressed as: from 1 ppm to 8440 ppm. This concentration of hydrolysed collagen in the beverages shall be reviewed regarding ready for consumption beverages or regarding beverages obtained after dilution by adding additional water in the prescribed proportion to produced concentrates in the form of powder or liquids. The functional ingredient hydrolysed collagen, also known as collagen peptides is produced through hydrolysis in controlled conditions of raw materials such as collagen sources from various animal origin.

The beverages containing hydrolysed collagen characterize with great diversity, depending on the other combined ingredients that they may include. Beverages may contain only hydrolysed collagen and water.

The water for producing the beverages may be tap water or spring or mineral water or water, gained by icebergs (glaciers). When tap water is used, the tap water shall mandatorily be supplied by central water supply system or extracted underground water or extracted from natural or artificially constructed ponds. Also, preventively or in case of need, the water can be additionally purified, or processed approved by the appropriate healthcare authority's methods of additional purification or processing: Examples of such methods are:

mechanical filtration through filtration systems,
filtration through chemically active filters to separate the unwanted salts of iron (Fe) and manganese (Mn),
decrease of total mineralization through ultrafiltration— using ultrafiltration (reverse osmosis systems;
decrease of total mineralization through filtration in ion exchange filter systems,
decrease of total mineralization through distillation of water (evaporation and further condensation), decontamination by UV-filter (UV-lamps),
decontamination by using chemical processing agents such as Chlorine($Cl_2$), Chlorine Dioxide($ClO_2$), Ozone ($O_3$), Active Oxygen($O_2$) and others.

Also water, used for the beverages may be additionally carbonated through adding Carbon Dioxide-$CO_2$. The quantity of the Carbon Dioxide added may reach 7,0 volume units (7,0 v/v). In the most common beverages combination it may usually vary between 0,5 and 5,0 v/v.

Beverages containing hydrolysed collagen may be produced by stabilizing preservatives. The preservatives used shall be permitted for use for the category of beverages. Respectively, the preservatives may be chemical substances (as Potassium Sorbate [E202], Sodium benzoate [E211] and others), which dissolute in the product and are only parts of its content or may be chemically active substances, used in the production of the product but subsequently dissolute to other ingredients (such as Dimethyl dicarbonate [E242]).

Beverages containing hydrolysed collagen may be produced without any preservatives as well as their stabilization in those cases is ensured through applying appropriate technological production methods. Such methods are for example:
  pasteurization of the product in combination with a "clean fill" and subsequent storage at refrigeration conditions,
  pasteurization of the product by UHT-sterilization followed by aseptic filling (filling in sterile environment) of the product;
  pasteurization of the product followed by hot filling of the product,
  filling of the product and further tunnel pasteurization ensuring reaching commercial sterility of the product;
  pasteurization of the product and using special nanomaterials when packaging the product in combination with further storage at refrigerator conditions.

In the process of filling the beverages, regardless of whether the beverage is produced by adding preservatives or with no added preservatives, packaging gases may be used and added in the package prior to filling, during the filling or after it. Packaging gases are gases, different than air, and are inert gases such as: Nitrogen [E941], Carbon dioxide [E290], Helium [E939] and others. These gases are added in the filling process with the purpose of protecting the product from adverse processes such as oxidation, change in taste, aroma and appearance. These gases contribute to ensuring the shelf life of the product while helping to preserve the quality of the added nutrients.

Regarding the appearance of the ready product, beverages containing hydrolysed collagen may be colourless or coloured, clear or cloudy and may contain a fine precipitate of larger particles on the bottom and/or to have uniformly dispersed particles in the liquid. They may be calm fluids or carbonated.

In other beverages containing hydrolysed collagen that may be coloured, various colourants may be added such as synthetic or organic ones from vegetable or animal origin, or may be from various fruit and/or vegetable concentrates, vegetable extracts. Added colourants, classified as additives with an E-number may be permitted for use in the beverage. The exact amount of coloring agent used will vary, depending on the agents used and the intensity desired in the finished product. Generally, if utilized, the coloring agent should be present at a level of from about 0.0001% to about 0.5%, from about 0.001% to about 0.1%, or from about 0.003% to about 0.2%, by weight or volume of the composition. Certain formulations will have no added colorant.

Beverages containing hydrolysed collagen may be produced unsweetened or sweetened through adding various sweeteners or mixtures of several ones.

Sweetening the present beverage may be done by adding sweeteners, most of which are low-calorie ones. Liquid as well as hard sweeteners may be used such as crystals or granules. Examples for sweeteners include:
  in a liquid form are the polyols: Sorbitols (E420), Xylitol [E967], Mannitol [E421], Maltitols [E965] and others,
  in a hard form are: Aspartame [E951], Cyclamates [E952], Neotame [E961], Acesulfame K [E950] and others, Sweetening beverages may be done by adding various types of sugars derived from natural sources. These sugars may be respectively non-refined or refined to a various extend. Examples of such sugars are: refined white sugar, unrefined or partly refined sugar, honey, fructose, glucose, glucose-fructose syrups, syrups derived from fruits, plant extracts.

The desired degree of sweetness of the present invention's beverage may vary from °Bx=1,0÷16,0 (brix units) or in cases when using artificial or natural low caloric sweeteners, the desired sweetness intensity shall match equivalences of °Bx=1,0÷16,0 for ready to drink beverages. One brix unit (°Bx) corresponds to 1% water aqueous sugar solution, i.e. 1,0 g sugar per 100 ml water.

For regulating the acidity and/or giving a sour taste of beverages containing hydrolysed collagen, fruit juices or fruit juice concentrates may be added. These fruit juices may have a sour taste, acidity regulating additives, or E-number additives such as, Citric acid [E330], Phosphoric acid [E338], Phosphates [E339; E340; E341, E343], Citrates [E331; E332; E333] and others. The titratable acidity of a preferred embodiments of the present invention's beverage containing hydrolysed collagen may be a value within the range of from about 0.01% w/v to about 0.85% w/v, about 0.1% w/v to about 0.45% w/v, 0.12% w/v to about 0.35% w/v or any ranges or single values within these ranges.

For beverages containing hydrolysed collagen, other ingredients may be added such as: thickeners and/or stabilizers. Thickeners are substances which increase the viscosity of a foodstuff. Stabilisers are substances which make it possible to maintain the physico-chemical state of a foodstuff. Stabilisers include substances which enable the maintenance of a homogenous dispersion of two or more immiscible substances in a foodstuff. Substances which stabilise retain or intensify an existing colour of a foodstuff and substances which increase the binding capacity of the food by the formation of cross-links between proteins. Example for ingredients used as thickeners and stabilizers are the substances: Gum arabic [E414], Guar gum [E412], Carrageenan [E407], Pectins [E440] and others.

For enhancing and modifying the intensity of taste of the present invention's beverage containing hydrolysed collagen, ingredients such as flavour enhancers may be added. These are substances which enhance the existing taste and/or odour of a foodstuff. Such are for example: Glutamic acid [E620], Guanylic acid [E626], Inosinic acid [E630] and others. For the purpose of adding flavour for taste, organic substances may be added to the present invention's beverage. Such organic substances include, for example: table salt, extracts and tinctures of plants, fruit, seeds, yeast extract and others.

Fruit and vegetable juices, fruit and vegetable purees, concentrates from fruit and vegetables as well as extracts or tinctures of fruit, part of fruit or plants may all be added to the present invention's hydrolysed collagen beverage or it may contain such substances. The diversity of this category of additives is high as it is conditioned on the natural diversity of plants. The juices, purees, concentrates or extracts that may be added to the present invention's beverage may be clear or cloudy, contain particles of fruit, vegetables or plants as seeds, parts of the peel, pulp, cells and so on. An example of clear juices that can be added to the present invention's beverage may be juices made from: apples, cherries, raspberries, strawberries, lemon, orange, grapefruit etc. Cloudy juices and purees can be produced from fruits: apple, sour cherry, raspberry, lemon, orange, plum, pear, apricot, peach, etc. In certain embodiments, the beverage containing hydrolysed collagen disclosed here may optionally include one or more juices (e.g., one or more of single-strength fruit, berry, or vegetable juice, as well as extracts, concentrates, purees, milks, and other forms) present at a level from about 0.0005% to about 99,16%, about 0.001% to about 20%, about 0.005% to about 15%, about 0.01% to about 10%, about 0.05% to about 5%, about 0.01% to about 10%, about 0.05% to about 5%, or about 0.1% to about 2.5% by weight of the beverage, or at a level of about 0.001%, 0.0025%, 0.005%, 0.0075%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10 11.0%, 12.0%, 13.0%, 14.0%, 15.0%, 16.0%, 17.0%, 18.0%, 19.0%, 20.0%, 21.0%, 22.0%, 23.0%, 24.0%, 25.0%, 26.0%, 27.0%, 28.0%, 29.0%, 30.0%, 31.0%, 32.0%, 33.0%, 34.0%, 35.0%, 36.0%, 37.0%, 38.0%, 39.0%, 40.0%, 41.0%, 42.0%, 43.0%, 44.0%, 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0 or about 99.16%, about by weight of the beverage, or any ranges or single values within these ranges. Typically, juice can be used, if at all, in an amount of from about 0.001% to about 45% by weight. Fruit and vegetable juices, fruit and vegetable purees, concentrates from fruit and vegetables as well as extracts or tinctures of fruit, part of fruit or plants may be mixed in all possible combinations with each other and then added to the present invention's hydrolysed collagen beverage For flavouring the present invention's beverage, aromas as well as ingredients with flavouring properties may be added. The beverage containing hydrolysed collagen disclosed here may optionally contain one or more flavourings or flavour compositions. For example, natural and/or synthetic fruit flavours, botanical flavours, other flavours, and mixtures thereof. Added concentrated aromas may be extracted from natural sources as: fruit, food, parts of plants, smoke and so on but may also consist of synthetic flavourings, approved for use with foodstuff. For flavouring the present invention's beverage, ingredients with flavouring properties such as herbs and spices extracts, fruit extracts and fruit concentrates with intense aroma may be used.

In certain embodiments, the present invention's hydrolysed collagen beverage disclosed here may optionally include one or more flavourings present at a level from about 0.0005% to about 5%, about 0.001% to about 4%, about 0.005% to about 3%, about 0.01% to about 2%, about 0.05% to about 1%, or about 0.1% to about 0.5% by weight of the beverage, or at a level of about 0.001%, 0.0025%, 0.005%, 0.0075%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9% or about 1.0% by weight of the beverage, or any ranges or single values within these ranges.

Vitamins and minerals with the purpose of enriching their nutritional value may be added to the present invention's beverage. Vitamins include, but are not limited to, Vitamin A, Vitamin D, Vitamin E, Vitamin K, Vitamin C, Thiamin (Vitamin $B_1$), Riboflavin (Vitamin $B_2$), Niacin (Vitamin $B_3$), Vitamin $B_6$, Folic acid (Vitamin $B_9$), Vitamin $B_{12}$, Biotin (Vitamin $B_7$), Pantothenic acid (Vitamin $B_5$). Minerals include, but are not limited to, Potassium (K), Chloride (Cl), Calcium (Ca), Phosphorus (P), Magnesium (Mg), Iron (Fe), Zinc (Zn), Copper (Cu), Manganese (Mn), Fluoride (F), Selenium (Se), Chromium (Cr), Molybdenum (Mo), Iodine (I). Supplements are typically present in amounts generally accepted under good manufacturing practices and are typically present in amounts between about 7.5% to about 100% RDV, where such RDV are established. But may present at a level from about 101% to about 150% RDV, about 120% to about 200% RDV, about 150% to about 300% RDV, about 200% to about 500% RDV.

Vitamins and minerals are used to enrich the beverage nutritional profile. For example, according to legislative food sources, a good source of Vitamin A can be found in substances such as: retinol, retinyl acetate, retinyl palmitate, beta-carotene. As Magnesium (Mg) sources used may be: magnesium carbonate, magnesium chloride, magnesium gluconate and etc. may be added to the present invention's beverage.

Enrichment of beverages with vitamins and minerals may be done with organic sources of vitamins and minerals. For example such vitamins are: acerola extracts, rose hips extracts and others, as organic sources of minerals used may be: organic concentrates by seawater, seaweed, eggshell extracts and others. The use of vitamins and minerals may vary to 100% and more than 100%, according to established Recommended Daily Value (RDV) for vitamins and minerals.

The present invention beverage containing hydrolysed collagen may be produced by adding appropriate electrolytes, often categorized as specialized beverage category, such as: isotonic sport beverages, hypertonic sport beverages, and hypotonic sport beverages.

Additional amino acids may be added to the present invention's beverage. Additional enrichment with amino acids may be done by adding amino acids in their L-forms. For example L-glutamine, L-isoleucine, L-leucine, L-valine, L-taurine and others may be added to the present invention's beverage. Additionally, amino acids may be added as separate amino acids as well as in combination to other amino acids.

Other types of proteins, different than collagen may be added to the present invention's hydrolysed collagen containing beverage. These proteins may be hydrolysed proteins with higher or lower molecular weight. For additional enrichment, other proteins may be added to the present invention, such as proteins from vegetable as well as animal origin proteins. For example, proteins from soy, peas, milk, egg and others may be added to the present invention's beverage.

Where other types of proteins and/or protein hydrolysates, other than collagen are added, the total concentration of binding proteins in the beverage should be varied, from 0.001 g/l g/L to 8.44 g/L, which may also be expressed as: 1 ppm to 8440 ppm. In these embodiments, the total protein concentration in the beverage is the sum of all protein sources contained in the beverages, including the added hydrolysed collagen.

Alternative embodiments of the present invention's beverage may be produced which do not contain lactose but may also include lactose as an individual ingredient or have added compositions which are sources of lactose.

The present invention's beverage may include additional added ingredients, such as dairy components which can be different fractions derived from milk. For example: whey proteins, casein, caseinates, etc.) or fractions derived from the colostrum (for example: antibodies, immunoglobulin, growth factors). Stated dairy components include, but are not limited to: lipids, proteins (casein, lactoglobulin), antibodies, minerals and salts (phosphates, calcium, magnesium, sodium, potassium, etc.), Vitamins (A, $B_6$, $B_{12}$, D, K, E, thiamine, niacin, biotin, pantothenic acid, etc.), carbohydrates (lactose), enzymes and others.

The present invention's beverage may be produced with other additives such as; fresh milk, reconstituted milk or milk fermented with lactic acid cultures and accordingly each of the following types of milk can be skimmed or whole to various extend. Fermented milk is usually derived from using the following starters: *Streptococcus thermophilus H Lactobacillus delbrueckii* subsp. *bulgaricus*, as well as various starters mostly from the *Lactobacillus, Lacto coccus, Bifidobacterium* and *Str. Thermophilus* kinds. During fermentation probiotic cultures may be added. Pre-prepared probiotic concentrates (probiotics) may also be added as individual ingredients to the present invention's beverage. The present invention's beverage containing hydrolysed collagen may also contain added prebiotic ingredients which are fibers which can be soluble as well as insoluble.

Various other ingredients with beneficial properties may be added to the present invention's beverage containing hydrolysed collagen. Such ingredients may add value to the present invention's beverage containing hydrolysed collagen. All these additional healthy ingredients may vary in different combinations as may be individually added to beverages containing hydrolysed collagen or be combined. Examples for such healthy ingredients are:

L-carnitine,
Coenzyme Q10,
Omega 3 and Omega 6 essential fatty acids,
Bee products, such as natural honey, bee pollen, royal jelly, propolis,
Vegetable extracts from plants with healthy effects that may include various parts of plants as: fruit, blossoms, peels, roots, stables. For example plants with healthy effects are: Panax Ginseng, Camomila, Lavender, Elettaria cardamomum, Ginkgo biloba and others,
Tea extracts (black, green, white etc.)
Soy isoflavones,
Hyaluronic acid and/or its salts,
Alpha Lipoic Acid,
Extracts of seaweed as well as purified finely ground seaweed,
Mushrooms extracts, edible and special types such as: Lentinula edodes, Grifola frondosa, Cordyceps Sinensis, Hericium erinaceus, Coprinus comatus and others,
Extracts of polyphenols—resveratrol, astaxanthin,
Carotenoids, including lutein and zeaxanthin,
Green coffee extracts,
Caffeine.

EXAMPLES OF PREFERRED EMBODIMENTS

Example 1 (as shown in Table 1) comprises a cloudy, coloured beverage containing hydrolysed collagen. The ingredients expressed in weight percentage are listed below in Table 1. Used ingredients are as follows: water purified by ultrafiltration technology, Hydrolysed bovine collagen Peptan® B 5000HD (Rousselot Inc.), crystalline fructose, peach aroma, citric acid [E330], antioxidant: ascorbic acid, acidity regulator: sodium citrates [E331], a powder mix of vitamins and minerals: D-pantothenate calcium; Pyridoxine hydrochloride; Hydroxocobalamin, D-biotin; Calcium gluconate; Magnesium gluconate; Zinc chloride, RDV levels: Pantothenic acid—15%; Vitamin $B_6$—15%; Vitamin $B_{12}$—15%; Biotin—15%; Ca—15%; Mg—15%; Zn—15%;), clear concentrated peach juice, carrageenan [E407], guar gum [E412], colour: carotenes. The beverage is aseptically filled into plastic disposable bottles 375 ml (12.680 fl. oz). It is sterilized in UHT-sterilizer at 137° C. for 4.2 seconds. It has a shelf life of 12 months when stored at 25° C., after opening shall be kept in the refrigerator up to 48 hours.

TABLE 1

| Ingredients: | % w/w in the Beverage |
|---|---|
| Water | 90.16 |
| Hydrolysed bovine collagen Peptan ® B 5000HD | 0.30 |
| Crystalline fructose | 7.50 |
| Peach aroma | 0.12 |
| Citric acid (E330) | 0.15 |
| Ascorbic acid (E300) | 0.05 |
| Sodium citrate (E331) | 0.10 |
| a powder mix of vitamins and minerals | 0.01 |
| Clear peach concentrate (65° Bx) | 1.50 |
| Carrageenan (E407) | 0.05 |
| Guar gum (E412) | 0.05 |
| Colour: carotenes (E160a) | 0.01 |
| Total: | 100% |

Example 2 (as shown in Table 2) comprises a clear, colourless beverage containing hydrolysed collagen. The ingredients, expressed in weight percentages, are listed below in Table 2. Used ingredients are as follows: water purified by ultrafiltration technology, Hydrolysed bovine collagen Peptan® B 5000HD (Rousselot Inc.). The beverage is aseptically filled into plastic disposable bottles 375 ml (12.680 fl. oz). It is sterilized in UHT-sterilizer at 137° C. for 4.2 seconds. It has a shelf life of 12 months when stored at 25° C., after opening shall be kept in the refrigerator up to 48 hours.

TABLE 2

| Ingredients: | % w/w in the Beverage |
|---|---|
| Water | 99.90 |
| Hydrolysed bovine collagen Peptan ® B 5000HD | 0.10 |
| Total: | 100% |

Example 3 (as shown in Table 3) comprises an opaque, coloured beverage, containing hydrolysed collagen. The compositions, expressed in weight percentages, are listed below in Table 3. Used ingredients are as follows: water purified by ultrafiltration technology, Hydrolysed fish collagen Peptan® F 2000HD (Rousselot Inc.), crystalline fructose, white crystal sugar, natural peach aroma, natural mango aroma, natural guava aroma, amidated pectin [E440ii], citric acid [E330], antioxidant ascorbic acid

[E300], acidity regulator: calcium lactate [E327], peach puree single strength, concentrated mango puree, colour: Riboflavins [E101]. The beverage is aseptically filled into disposable plastic bottles 375 ml (12.680 fl. oz). It is homogenized at 150 bar and sterilized in UHT-sterilizer at 137° C. for 4.2 seconds. It has a shelf life of 12 months when stored at 25° C., after opening shall be kept in the refrigerator up to 48 hours.

TABLE 3

| Ingredients: | % w/w in the Beverage |
| --- | --- |
| Water | 82.53 |
| Hydrolysed fish collagen Peptan ® F 2000HD | 0.40 |
| Crystalline fructose | 6.00 |
| White crystal sugar | 4.50 |
| Peach aroma | 0.10 |
| Mango aroma | 0.15 |
| Guava aroma | 0.05 |
| Citric acid (E330) | 0.16 |
| Ascorbic acid (E300) | 0.05 |
| Calcium lactate (E327) | 0.15 |
| Amidated pectin (E440ii) | 0.20 |
| Peach puree (10° Bx) | 4.50 |
| Mango puree (32° Bx) | 1.20 |
| Colour: Riboflavins (E101) | 0.01 |
| Total: | 100% |

Example 4 (as shown in Table 4) comprises a transparent, coloured beverage containing hydrolysed collagen. Ingredients expressed in weight percentage, are listed below in Table 4. Used ingredients are as follows: water purified by ultrafiltration technology, Hydrolysed fish collagen Peptan® F 2000HD (Rousselot Inc.), crystalline fructose, brown sugar, natural strawberry aroma, natural lime aroma, natural dry green tea extract, citric acid [E330], acidity regulator: sodium citrates, clear strawberry juice concentrate, colour: chlorophyllins [E141]. The beverage is aseptically filled into plastic disposable bottles 375 ml (12.680 fl. oz). It is sterilized in UHT-sterilizer at 137° C. for 4.2 seconds. It has a shelf life of 12 months when stored at 25° C., after opening shall be kept in the refrigerator up to 48 hours.

TABLE 4

| Ingredients: | % w/w in the Beverage |
| --- | --- |
| Water | 90.33 |
| Hydrolysed fish collagen Peptan ® F 2000HD | 0.40 |
| Crystalline fructose | 3.00 |
| Brown sugar | 5.50 |
| Strawberry aroma | 0.15 |
| Citrus (lime) aroma | 0.05 |
| Dry natural green tea extract | 0.15 |
| Citric acid (E330) | 0.14 |
| Sodium citrates (E331) | 0.05 |
| Clear strawberry concentrate (65° Bx) | 0.20 |
| Colour: chlorophyllins (E141) | 0.03 |
| Total: | 100% |

Example 5 (as shown in Table 5) comprises an opaque, coloured beverage containing hydrolysed collagen. The ingredients, expressed in weight percentages, are listed below in Table 5. Used ingredients are as follows: water purified by ultrafiltration technology, Hydrolysed bovine collagen Peptan® B 5000HD (Rousselot Inc.), soy protein isolate SUPRO® PLUS 2640 DS (DANISCO), natural mango aroma, natural ripe apple aroma, amidated pectin [E440ii], brown cane sugar, citric acid [E330], antioxidant: ascorbic acid [E300], acidity regulator: calcium lactate [E327], apple puree single strength, saffron extract. The beverage is aseptically filled into disposable plastic bottles 375 ml (12.680 fl. oz). It is homogenized at 150 bar and sterilized in UHT-sterilizer at 137° C. for 4.2 seconds. It has a shelf life of 12 months when stored at 25° C., after opening shall be kept in the refrigerator up to 48 hours.

TABLE 5

| Ingredients: | % w/w in the Beverage |
| --- | --- |
| Water | 83.98 |
| Hydrolysed bovine collagen Peptan ® B 5000HD | 0.30 |
| Soy protein isolate SUPRO ® PLUS 2640 DS | 0.45 |
| Mango aroma | 0.10 |
| Apple aroma | 0.15 |
| Amidated pectin (E440ii) | 0.20 |
| Brown sugar | 9.00 |
| Citric acid (E330) | 0.12 |
| Ascorbic acid (E300) | 0.05 |
| Calcium lactate (E327) | 0.13 |
| Apple puree (10.5° Bx) | 5.50 |
| Saffron extract | 0.02 |
| Total: | 100% |

A preferred alternative embodiment of the present invention's beverage comprises a clear, colourless beverage containing hydrolysed collagen, with vitamins and minerals as shown in Table 6.

TABLE 6

| Ingredients: | % w/w in the Beverage |
| --- | --- |
| Water | 96.15 |
| Hydrolysed bovine collagen Peptan ® B 5000HD | 0.29 |
| Crystalline fructose | 3.44 |
| Givodan ® Peach nectarine flavour "99278-DO" | 0.04 |
| Citric acid (E330) | 0.12 |
| * a powder mix of vitamins and minerals | 0.37 |
| Total: | 100% |

* Vitamin Premix Material-No. UF40105368; produced by DSM Nutritional Products Europe Ltd. The Vitamin Premix to covers 15% RDA/100 ml of: Vitamin B12, Mg and Zn.

An alternative preferred embodiment of the beverage comprises a clear, colourless beverage containing hydrolysed collagen, with vitamins and minerals as shown in Table 7.

TABLE 7

| Ingredients: | % w/w in the Beverage |
| --- | --- |
| Water | 96.10 |
| Hydrolysed bovine collagen Peptan ® B 5000HD | 0.29 |

TABLE 7-continued

| Ingredients: | % w/w in the Beverage |
|---|---|
| Crystalline fructose | 3.44 |
| Givodan ® Elder-flower flavour "L-18646" | 0.04 |
| Givodan ® Cucumber flavour "L-130672" | 0.05 |
| Citric acid (E330) | 0.12 |
| * a powder mix of vitamins and minerals | 0.37 |
| Total: | 100% |

* Vitamin Premix Material-No. UF40105368; produced by DSM Nutritional Products Europe Ltd. The Vitamin Premix to covers 15% RDA of: Vitamin B12, Mg and Zn.

An alternative preferred embodiment of the beverage comprises a clear, colourless beverage containing hydrolysed collagen, with vitamins and minerals as shown in Table 8.

TABLE 8

| Ingredients: | % w/w in the Beverage |
|---|---|
| Water | 96.47 |
| Hydrolysed bovine collagen Peptan ® B 5000HD | 0.29 |
| Crystalline fructose | 3.44 |
| Givodan ®Ginger &Lemon flavour "L-147773" | 0.05 |
| Citric acid (E330) | 0.12 |
| * a powder mix of vitamins and minerals | 0.04 |
| Total: | 100% |

* Vitamin Premix Material-No. UF40107368; produced by DSM Nutritional Products Europe Ltd. The Vitamin Premix to covers 15% RDA of: Vitamin B12, Vitamin B7 and Zn.

An alternative preferred embodiment of the beverage comprises a clear, colourless beverage containing hydrolysed and mineral water as shown in Table 9.

TABLE 9

| Ingredients: | % w/w in the Beverage |
|---|---|
| *Mineral water | 99.84 |
| Hydrolysed bovine collagen Peptan ® B 2000HD | 0.1 |
| Phosphoric acid [E338] | 0.059 |
| Total: | 100% |

*The mineral water has the following characteristics:
Electrical conductivity at 20° C.(μS/cm): 493.5;
Potassium ($K^+$), mg/l: 0.60;
Magnesium ($Mg^{2+}$), mg/l: 28.0;
Calcium ($Ca^{2+}$), mg/l: 77.30;
Ammonium ($NH^+$), mg/l: <0.05;
Bicarbonate ($HCO_3^-$), mg/l: 270.0;
Chloride ($Cl^-$), mg/l: 4.60;
Sulphate ($SO_4^{2-}$), mg/l: 65.80;
dry residue at 180° C., mg/l: 340.3

Preferred Method of Preparation:

The drink is obtained in the following method. The preliminary hydrolyzed collagen dissolution takes place in a container, made of stainless steel, with a maximal capacity 2500 l or others), equipped with a stirrer and a flow heater on the way of the supplied water. The water in the container warms to a temperature: (min. 60° C.÷max. 90)±5° C. through the flow heater. The container stirrer starts working. The preliminary weighed amount of collagen in powder form is fed to the mixing chamber of a mixing unit, which automatically receives the fed powdery collagen, wets it uniformly with water, which circulates between the mixing unit and the mixing container, sucks it by means of vacuum effect and forwards it to the container for preliminary dissolution. This process takes at least 5 minutes. Thereupon the mixing unit is stopped, i.e. the circulation between the mixing container and the mixing unit is discontinued. The obtained preliminary solution of hydrolyzed collagen in a definite ratio with water is stirred additionally by the stirrer of the container for preliminary dissolution. The stirring takes at least 10 minutes.

The obtained preliminary concentrated dissolution of hydrolyzed collagen is subject to filtration through filter sleeves with permeability at least 20 μm. The concentrated solution is supplied through a pump to a filter unit, after which it is forwarded to a second mixing container, made of stainless steel, with a maximal capacity 10500 l for preparation of the drink itself.

After completion of the filtration, the concentrated solution is transferred to the second mixing container. The second container is equipped with two stirrers—lower stirrer for a low level and an upper stirrer, as well as with an automatic level gauge, which reads off the actual liquid volume, while the level gauge gives a signal to the stop valve, dosing drink water to the container. The lower stirrer starts working automatically after the liquid level in the second mixing container reaches up to 2000 l. Drinking water is added to the available quantity of 2000 l solution upon already working lower stirrer, and when the liquid level in the second mixing container reaches up to 4500 l, the upper stirrer also starts working automatically.

For other stock keeping units (or SKU's) where the beverage contains except collagen other ingredients such as: flavorings, vitamins, minerals etc . . . . All additional ingredients, previously precisely measured, dissolved similarly to the collagen solution in a 1000 l water for example, but with the temperature (6÷25° C.). This reconstituted solution is transferred in the same way as already transferred collagen solution. Adding of drinking water with the temperature (6÷25° C.) continues until the level gauge reads off 10000 l. Subsequently, the level gauge automatically gives a signal to the stop valve and the water feeding is discontinued. The stirring of the solution upon simultaneous operation both of the upper and the lower stirrer continues minimum 10 minutes. Thereafter the upper stirrer is stopped and the ready drink is let to be stirred only by the lower stirrer.

The ready drink represents a solution of hydrolyzed collagen with concentration of 10 kg per 10000 l water, i.e. 1 g/l (1000 mg/l). This stirring continues and the drink is forwarded for sterilization and filling. When the liquid level in the second mixing container subsides under 2000 l due to the continuous taking out of the product to the sterilizer of the filling line, this stirrer stops automatically. Before forwarding for sterilization and filling the ready drink has to be analyzed in order the quality property of the drink to be confirmed. For that purpose a sample of the ready drink is taken through a faucet, which the second mixing container is equipped with. This sample is tested at a production laboratory about the conformity of the standardized indices regarding: appearance, clarity, smell and flavor. In case of confirming evaluation the ready drink can be forwarded to the filling block.

The tested drink is fed to a sterilizing block, which is located before the filling and closure block. The drink is sterilized, which ensures a microbiological stability against spoilage and worsening of its characteristics. Since the used raw material of drinking water and hydrolyzed collagen is not sterile and the process of preliminary dissolution and final dissolution to a standard drink itself is performed in a non-sterile environment, it is supposed, that the ready drink is polluted with microorganisms. A sterilization, which is known under the trade name UHT—sterilization, is applied at ultra-high temperature for a short time (some seconds). This sterilization process guarantees the termination of the active cells microorganisms, ensuring the commercial sterility of the ready product. Furthermore, the stabilized by such kind of sterilization ready drink can be transported, exposed at commercial premises and sold at room temperature, i.e. it is not necessary to support a cold chain, offering uninterrupted transport and distribution of the products under refrigeration conditions. The so called UHT sterilization allows maximally to preserve the usefulness of the active ingredients of the drink, while the freshness of the natural and original taste and flavor are kept and the appearance of taste defects is avoided.

The drink comes into the first section of a pasteurizer—sterilizer, which comprises three sections: for heating, for maintaining the temperature and for cooling. Each of the three sections is equipped with fully insulated double-rooms, which indirectly contact each other through a tight separating heat-exchange surface. The drink, coming into the first preheating section, meets in an indirect reverse flow the already treated drink, which leaves the maintaining section. In this way an energy savings is ensured, while the incoming drink absorbs a part of the heat of the leaving drink. The preheating of the incoming drink facilitates and guarantees the easily and effective prompt achievement of the desired temperature of maintenance—the actual sterilization, which is performed in the maintaining section. In the maintaining section the drink meets in an indirect reverse flow (through the heat-exchange surface) the heat medium—a hot steam. The inputted sterilizing temperature and the maintenance time (stay in the maintaining section) are controlled automatically by means of computer system. After the time of maintenance at the inputted sterilizing temperature is over, the drink automatically is pushed into the preheating section, in order to meet again in a reverse flow the incoming drink and to give a part of its heat. Subsequently, the already semi-cooled sterilized drink comes into the cooling section, where its final refrigeration takes place by means of ice-cold water in a reverse flow, until the desired given temperature of filling the drink is reached.

The recommendable mode of UHT sterilization of the drink is:
  sterilization at temperature 137° C. and maintenance for 4,2 s under 13000 l/h flow rate; (it's possible these parameters to fluctuate according to the production/filling line characteristics)
  the sterilized cooled product leaves the sterilizer at temperature 20° C.

The filling of the ready sterilized drink is performed by means of an aseptic filling and closure mono-block. The filling takes place in a closed sterile system in order to prevent the eventual pollution. The filling is performed under controlled conditions by means of sterile compartments, while each of them is cleaned through chemical detergents and is sterilized in advance.

A definite pressure of sterile air is maintained and each filling block section has anti-bacterial filters, which preserve the machine from microbiological pollution during the filling process. The maintained pressure difference (the sterile air pressure is bigger) ensures a barrier, which doesn't allow the entering of non-sterile air. The insulation from the environment is also guaranteed by means of a liquid seal (disinfectant). The disinfectant represents a liquid barrier between the inside of the sterilizing, the filling and the closing carousel and the environment, and protect the machine against microbiological contamination.

The bottles where the product is filled in, are prepared after blowing from blanks—PET performs. The bottles are forwarded into the aseptic filling and closure block by means of a pneumatic belt conveyor. The blowing process of bottles by prompt ultra-heating at high temperature about 140° C. is performed just before their feeding to the filling and closure block, which guarantees the clean packaging. The packs are sterilized finally before filling by spraying with a hydrogen peroxide solution and a subsequent prompt drying by means of sterile, dry and warm air. The caps, which are used for the pack closure, are also sterilized in a compartment for a preliminary sterilization of caps. The sterilization of bottles and caps (also called "dry sterilization") is performed at temperatures: 140° C. (for bottles) and 150° C. accordingly (for caps) in two steps:
  VHP—injection (of hydrogen peroxide in evaporated phase);
  activation and drying with dry, sterile air.

The cooled drink for filling is forwarded at temperature 20° C. and is non-contact filled (there is no physical contact between the bottle and the filling valve during the dosage of the product). The temperature and the flow of the drink, fed for filling, are controlled automatically during the filling process. The filling of the drink is performed in nitrogen environment, ensuring an inert atmosphere, which additionally preserves the product from oxidation during the storage period. The closed and labeled bottles are packed in stacks by means of a foil machine. The stacks are palletized automatically and the ready pallets are forwarded to the storage area.

While this disclosure refers to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the spirit thereof.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements. Therefore, it is intended that the disclosure not be limited to the particular embodiments disclosed.

What is claimed is:
1. A beverage comprising:
  water;
  collagen in a concentration range of about 0.001 grams per liter to 8.44 grams per liter;
  a vegetable juice in an amount of 0.001% to about 45% by weight or a vegetable juice concentrate;
  ascorbic acid in an amount that is about 0.05% by weight;
  citric acid in an amount that is about 0.12% by weight; and
  at least one additive, wherein the at least one additive comprises a stabilizing preservative and at least one other protein with a concentration range sum total of about 0.0001 grams per liter to 8.44 grams per liter, and wherein the beverage is pasteurized.

2. The beverage of claim 1, wherein the beverage further comprises a packaging gas.

3. The beverage of claim 1, wherein the beverage further comprises a colorant.

4. The beverage of claim 3, wherein the colorant is synthetic or organic and derived from vegetable, fruit or animal origin.

5. The beverage of claim 3, wherein the colorant is in a concentration range of at least one of 0.0001-% to about 0.05-%, 0.001% to about 0.1-%, and 0.003% to about 0.2-%.

6. The beverage of claim 3, wherein the colorant is in a concentration range of at least one of 0.05% to about 0.0001%, 0.1% to about 0.001-%, and 0.2% to about 0.003%.

7. The beverage of claim 1, wherein the beverage further comprises a sweetener.

8. The beverage of claim 7, wherein the sweetener is selected from the group consisting of liquid form, hard form, natural sugars, refined sugars, low caloric, and non refined sugars.

9. The beverage of claim 1, further comprising at least one additional acidity regulating or E-number additive.

10. The beverage of claim 1, wherein the beverage further comprises a thickener.

11. The beverage of claim 1, wherein the beverage further comprises a stabilizer.

12. The beverage of claim 1, wherein the beverage further comprises a flavor enhancer.

13. The beverage of claim 1, further comprising at least one additional vitamin.

14. The beverage of claim 1, wherein the beverage further comprises a mineral.

15. The beverage of claim 1, wherein the beverage further comprises an electrolyte.

16. The beverage of claim 1, wherein the beverage further comprises an amino acid.

17. The beverage of claim 1, wherein the beverage further comprises a dairy component.

18. The beverage of claim 1, wherein the beverage further comprises a probiotic ingredient.

19. The beverage of claim 1, wherein the beverage further comprises a prebiotic ingredient.

20. The beverage of claim 1, wherein the beverage further comprises an extract.

21. The beverage of claim 1, further comprising about 0.13% calcium lactate.

* * * * *